(12) United States Patent
Harvey et al.

(10) Patent No.: US 9,517,987 B1
(45) Date of Patent: Dec. 13, 2016

(54) RENEWABLE BISPHENOLS AND RESINS FROM SALICYLIC ACID

(71) Applicant: The United States of America as represented by the Secretary of the Navy, Washington, DC (US)

(72) Inventors: Benjamin G. Harvey, Ridgecrest, CA (US); Heather A. Meylemans, Ridgecrest, CA (US); Michael E. Wright, Ridgecrest, CA (US); Andrew Chafin, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/692,362

(22) Filed: Apr. 21, 2015

Related U.S. Application Data

(60) Provisional application No. 61/982,106, filed on Apr. 21, 2014.

(51) Int. Cl.
| | |
|---|---|
| *C08G 64/20* | (2006.01) |
| *C08G 64/24* | (2006.01) |
| *C08G 64/28* | (2006.01) |
| *C07C 37/20* | (2006.01) |
| *C07C 37/00* | (2006.01) |
| *C08G 64/30* | (2006.01) |
| *C08G 73/00* | (2006.01) |
| *C08L 69/00* | (2006.01) |
| *C08K 7/14* | (2006.01) |
| *C08K 7/06* | (2006.01) |

(Continued)

(52) U.S. Cl.
CPC ............ *C07C 37/20* (2013.01); *C07C 37/002* (2013.01); *C07C 39/16* (2013.01); *C08G 64/06* (2013.01); *C08G 64/24* (2013.01); *C08G 64/28* (2013.01); *C08G 64/307* (2013.01); *C08G 73/00* (2013.01); *C08K 7/06* (2013.01); *C08K 7/14* (2013.01); *C08L 69/00* (2013.01); *C08L 79/00* (2013.01)

(58) Field of Classification Search
CPC ...................................................... C08G 64/20
USPC .......................................... 528/86, 196, 422
See application file for complete search history.

(56) References Cited

PUBLICATIONS

Kadla, John F. et al, "The Reactions of Lignins with High Temperature Hydrogen Peroxide", Holzforschung (1999) pp. 277-284, vol. 53.

(Continued)

*Primary Examiner* — Duc Truong
(74) *Attorney, Agent, or Firm* — Charlene A. Haley; Stuart H. Nissim

(57) ABSTRACT

A method for the selective synthesis of bisphenols, thermosetting resins, and thermoplastics from salicylic acid, the major component of wintergreen oil, and a viable target for engineered biosynthesis. Condensation of salicylic acid, structural analogs of salicylic acid, and derivatives of salicylic acid with short chain aldehydes or ketones and subsequent decarboxylation has the potential to produce bisphenols that are direct replacements for conventional resins, while the steric and electronic effects of salicylic acid improve the efficiency and selectivity of the conversion process. The utilization of renewable polyphenols as precursors to epoxies, poly carbonates, and high temperature thermosets including cyanate esters, provides an opportunity to develop full-performance resins while reducing the use of petroleum based feedstocks. This approach will then diminish the overall environmental impact of resin production while allowing for a sustainable source of phenols.

17 Claims, 4 Drawing Sheets

(51) Int. Cl.
    *C07C 39/16*         (2006.01)
    *C08L 79/00*         (2006.01)
    *C08G 64/06*         (2006.01)

(56) References Cited

PUBLICATIONS

Philip, Jose et al, J.Med.Chem. (1965) p. 405 vol. 8 (3).

US 9,517,987 B1

RENEWABLE BISPHENOLS AND RESINS FROM SALICYLIC ACID

CROSS-REFERENCE TO RELATED APPLICATIONS

This is a non-provisional application, claiming the benefit of, parent provisional patent application Ser. No. 61/982,106 filed on Apr. 21, 2014, the entire disclosure of which is incorporated herein by reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to the efficient synthesis of high performance thermoplastics, resins, and composite materials from an abundant renewable source.

BACKGROUND OF THE INVENTION

Bisphenol compounds, including Bisphenol A (BPA), are widely used as building blocks for a variety of commercial, industrial, and military products. Specifically, bisphenols are the building blocks for polycarbonate plastics, epoxy resins, polyester resins, and cyanate ester resins for example. BPA-derived plastics have been commercially produced since the 1950s, and have become important because of their shatter resistance, thermal resistance, electrical resistance, and optical clarity. Polycarbonate plastics are found in a wide range of products, including eyeglass lenses, CDs and DVDs, computers, appliances, power tools, sports equipment, medical devices, as well as food and drink containers. Epoxy resins are easily formed from BPA and are resistant to chemicals, which makes them useful in products such as printed circuit boards, paints, adhesives, and coatings for the inside of metal cans. While polycarbonates and epoxy resins are the major applications for bisphenol A, other uses include flame retardants, unsaturated polyester resins, polysulfone resins, polyetherimide resins and polyarylate resins.

More than 850,000 tons of BPA were consumed in the U.S. in 2003; 72% of which was used to make polycarbonate plastic and 21% going into epoxy resins. During 2013-2018, the total world consumption is expected to grow at an average annual rate of 4.2%. Currently BPA is synthesized by the condensation of acetone (signified by the suffix A in the name) with two equivalents of phenol. The reaction is catalyzed by a strong acid, such as hydrochloric acid (HCl) or a sulfonated polystyrene resin.

Commercially available bisphenol compounds, especially polyaromatic bisphenols, are derived from petroleum, a limited resource. What is needed is a renewable source of these bisphenol compounds to meet the growing demand. Research into bio-derived materials for plastic and resin precursors is extremely active. The current invention provides a renewable, bio-derived source for BPA and analogues. In an effort to create more sustainable bisphenol building blocks the current method provides for the selective synthesis of bisphenols from salicylic acid, the major component of wintergreen oil, and a viable target for engineered biosynthesis. As a tangential benefit, renewable phenols may have significantly lower toxicity than typical precursors of bisphenol A.

U.S. Pat. No. 5,770,658 (Baudoul, et al.) describes the reaction of an epoxy resin with an alkyl or alkenyl substituted hydroxyl substituted aromatic acid (e.g. salicylic acid) or compounds derivable from salicylic acid (such as cresol) to produce resins for coating and civil engineering applications. U.S. Pat. No. 5,936,057 (Baudoul, et al.) similarly describes epoxy resin mixtures with alkylated salicylic acid. These patents describe the use of salicylic acid to modify resins but not the direct use of salicylic acid as the starting product to make polyphenols and their resulting plastics and resins.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

Renewable polyphenols derived from salicylic acid, its analogues, and its derivatives can be converted to thermoplastics and resins with uses across a wide range of both commercial and military platforms. Increased use of lightweight plastics and composites decreases overall fuel usage, reducing transportation and commerce costs. Deriving these plastics and composites from renewable sources reduces dependency on petroleum sources for structural materials. The current invention utilizes sustainable phenolic building blocks in the selective synthesis of bisphenols from salicylic acid, the major component of wintergreen oil, its analogues, and its derivatives, which are viable targets for engineered biosynthesis or can be generated by the oxidation of lignin.

Figure 1:
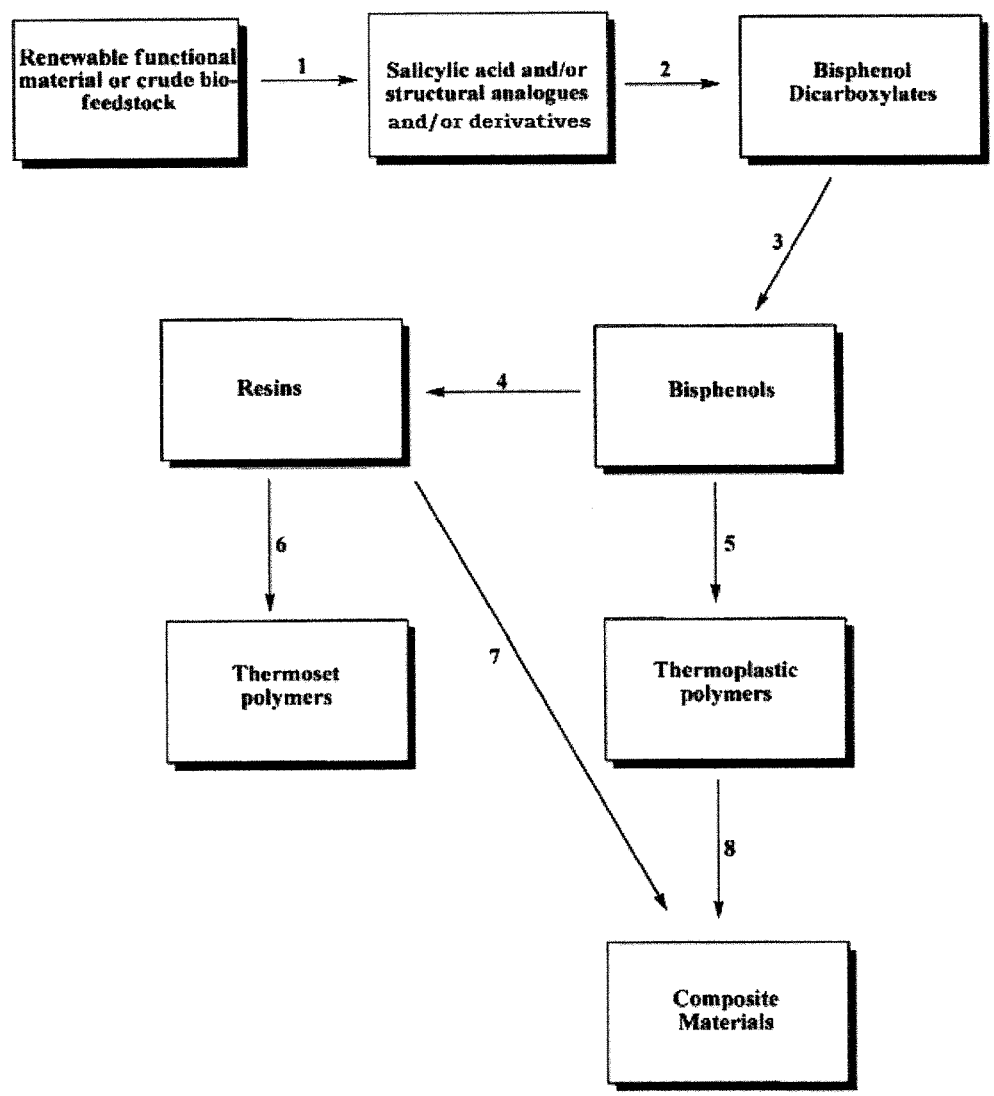
FIG. 1 is an illustration of synthetic schemes for producing resins, thermoplastics, and composite materials from bisphenols synthesized using renewable phenols according to embodiments of the invention.

Embodiments of the invention include the following tasks shown in FIG. 1: Task 1: A renewable phenol is derived/isolated from a natural, renewable source, e.g. extraction of wintergreen oil (methyl salicylate) from feedstock, the oxidation of lignin, or produced via a biosynthetic route (engineered biosynthesis), for example; Task 2: A renewable phenol (e.g. salicylic acid, structural analogues of salicylic acid, derivatives of salicylic acid, o-cresol) is converted to a polyphenol or polyphenol dicarboxylate through condensation with an aldehyde or ketone using either Bronsted or Lewis acids, in either a homogenous or heterogeneous fashion; Task 3: Depending on the properties of the polyphenol, the molecule is selectively modified through elimination and/or hydrolysis to yield an altered polyphenol; Task 4: Polyphenols prepared in Task 3 are converted to a variety of resins (e.g. cyanate esters, epoxies); Task 5: Alternatively, polyphenols prepared in Task 3 are directly converted to thermoplastics such as polycarbonates; Task 6: In specific cases, resins prepared in Task 4 are polymerized to form thermoset polymers; Task 7: Resins prepared in Task 4 are combined with fibers (e.g. glass, carbon) or other support materials and cured through various methods to produce a composite material; Task 8: Thermoplastics produced in Task 5 are either utilized in a pure form or are combined with a support material to produce a composite.

Other embodiments of the invention include the following tasks: Task 1: A biphasic According to one preferred method of the present invention, condensation of salicylic acid with carbonyl reactants, preferably short chain aldehydes or ketones, produces polyphenols that can be decarboxylated and then used as direct replacements for conventional, petroleum based polyphenols. An additional benefit of this process is that the steric and electronic effects of salicylic acid improve the efficiency and selectivity of the condensation process. The utilization of renewable polyphenols as precursors to materials such as: cyanate esters; resins; epoxies; polycarbonates and other thermoplastics including polyethers, poly ether ether ketones (PEEK), polyarylates, and polyesters; high temperature thermosets; epoxy resins; and benzoxazines, provides an opportunity to develop full-performance resins, plastics and the like while reducing the use of petroleum based feed stocks. This approach will then diminish the overall environmental impact of resin production while allowing for a sustainable source of phenols.

A basic synthesis of polyphenols according to the present invention comprises the first 3 tasks:

Task 1: Ortho-substituted phenol sources, (e.g. salicylic acid, structural analogues of salicylic acid, derivatives of salicylic acid, and o-cresol), are prepared or isolated from a renewable source (e.g. lignin, wintergreen oil (methyl salicylate)), or produced via a biosynthetic route;

Task 2: The ortho-substituted phenol is condensed with a carbonyl reactant, e.g. an aldehyde or ketone, utilizing an acid catalyst to produce a polyphenol or polyphenol dicarboxylate coupled at the position para to the hydroxyl groups of the phenols; and, Task 3: The resulting polyphenol is then decarboxylated as needed. Any carboxyls present on the polyphenol are: a) reduced and/or b) hydrogenated; resulting in the conversion of each carboxyl group to either hydrogen or a methyl group, to yield a polyphenol.

In the process of the present invention, a salicylic acid-based, ortho-substituted phenol (in Task 2) may be decarboxylated before condensation with the carbonyl reactants to produce the polyphenols (Task 3). One such example is the reduction of salicylic acid to o-cresol and then using the o-cresol in the condensation Task 3.

As described in Tasks 4 through 8, these polyphenols can further be converted to polymers, for example: resins; epoxies; polycarbonates; other thermoplastics including polyethers, poly ether ether ketones (PEEK), polyarylates, polyesters, epoxides, polysulfones, polyester-styrene, alkylphenolic polymers, polyoxalates, and polyalylates; high temperature thermosets; cyanate esters; epoxy resins; or benzoxazines via the same processes used with petroleum-based polyphenols.

Task 1:

Salicylic acid, the active extract of the bark of the white willow (*Salix Alba*), is biosynthesized from the amino acid phenylalanine. In other species of tree it can also be synthesized via a phenylalanine-independent pathway.

Salicylic acid, its analogues, and its derivatives can be isolated from a number of natural sources using processes known in the art such as, but not limited to, the following examples.

Salicylic acid can be obtained via oxidation of plant lignin. One such method comprises subjecting lignin to alkaline hydrogen peroxide oxidation in the presence of DTMPA (diethylenetriaminepentamethylene-pentaphosphonic acid) and molecular oxygen at various temperatures as described by Kadla, John F. et al, "The Reactions of Lignins with High Temperature Hydrogen Peroxide", Holzforschung 53 (1999) 277-284.

Salicylic acid can also be obtained using a maceration process. Raw plant materials are soaked in solvents like water or alcohol. A thick extract or resinous substance is obtained at the end of the process by removing the solvent.

Salicylic acid can also be prepared by the hydrolysis of methyl salicylate (oil of wintergreen) or aspirin (acetylsalicylic acid) with a strong acid or base. Methyl salicylate can be distilled from the twigs of *Betula lenta* (sweet birch) and *Gaultheria procumbens* (eastern teaberry or wintergreen). *Spiraea* plants also contain methyl salicylate in large amounts and are used similarly to wintergreen.

Oil of wintergreen can be obtained by steam distillation of the leaves of the plant following maceration in warm water, for example. Solvent extraction can be used for extraction of oil from the plants. For this process, hydrocarbon solvents, e.g. ether, are used.

Task 2

Figure 2:
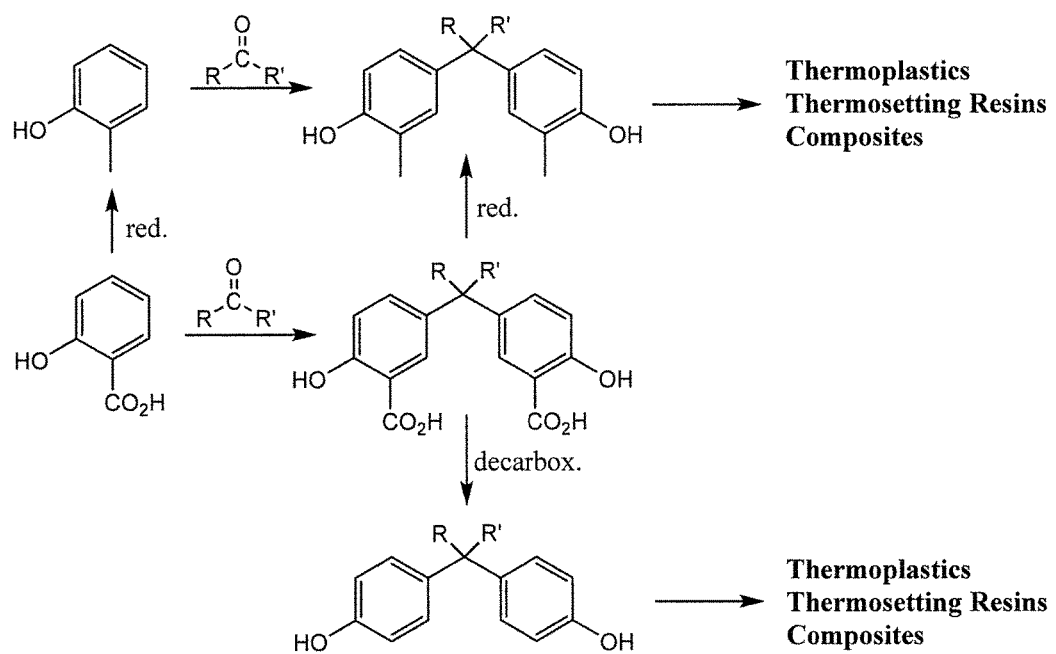
FIG. 2 is an illustration of synthetic schemes for producing resins, thermoplastics, and composite materials from bisphenols of functionalized salicylic acid synthesized from renewable phenol sources according to embodiments of the invention.

The formulae schemes shown in FIG. 2 illustrate some basic methods of the current invention for producing polyphenols and polymers from renewable sources. A preferred embodiment comprises the condensation of salicylic acid, its analogue, or its derivative, with a carbonyl, for example an aldehyde or ketone, having the formula:

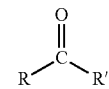

where R and R' of said carbonyl reactant are independently selected from the group consisting of hydrogen, alkyl having from 1-100 carbon atoms, substituted alkyl having from 1-100 carbon atoms, alkene having from 1-100 carbon atoms, substituted alkene having from 1-100 carbon atoms, alkenyl having from 1-100 carbon atoms, substituted alkenyl having from 1-100 carbon atoms, alkynyl having from 1-100 carbon atoms, substituted alkynyl having from 1-100 carbon atoms, alkyne having from 1-100 carbon atoms, substituted alkyne having from 1-100 carbon atoms, cyclic alkyl, substituted cyclic alkyl, aromatic, or substituted aromatic, or R and R' are mutually part of a ring system such as a cyclic ketone, e.g., cyclohexanone;

to form a polyphenol dicarboxylate or other carboxylated oligomer. Varying the ratio of phenol:carbonyl determines the resulting polyphenol/oligomer. A phenol:carbonyl ratio of 2:1 will yield a bisphenol; 3:1 will yield a trimer, etc.

In another embodiment, salicylic acid is converted to o-cresol which is then followed by the condensation of cresol with short chain aldehydes or ketones, forming a polyphenol,

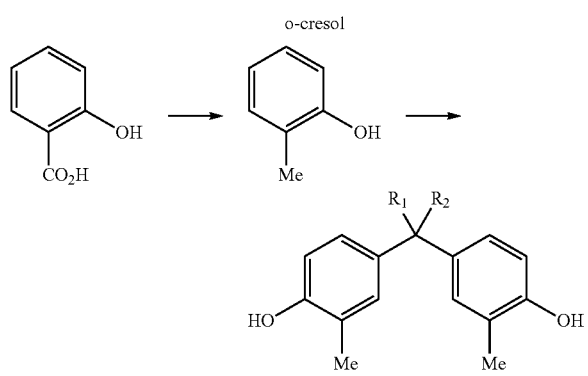

where R and R' of said carbonyl reactant are independently selected from the group consisting of hydrogen, alkyl having from 1-100 carbon atoms, substituted alkyl having from 1-100 carbon atoms, alkene having from 1-100 carbon atoms, substituted alkene having from 1-100 carbon atoms, alkenyl having from 1-100 carbon atoms, substituted alkenyl having from 1-100 carbon atoms, alkynyl having from 1-100 carbon atoms, substituted alkynyl having from 1-100 carbon atoms, alkyne having from 1-100 carbon atoms, substituted alkyne having from 1-100 carbon atoms, cyclic alkyl, substituted cyclic alkyl, aromatic, or substituted aromatic, or where R and R' are mutually part of a ring system such as a cyclic ketone, e.g., cyclohexanone, for example.

The following are examples of the process and are not limited to the following steps in any specific order (unless otherwise stated). Any prophetic examples are for illustration purposes only and not to be used to limit any of the embodiments.

Example 1

One equivalent of a carbonyl reactant is condensed with two equivalents of a renewable ortho-substituted phenol, for example salicylic acid, utilizing at least one homogenous or heterogeneous acid catalyst and heat to form a polyphenol. In some cases, depending on substituents, this condensation can be performed without heat, at ambient or low temperature. The dicarboxylate is then decarboxylated to yield a polyphenol.

Example 2

In the process of Task 2, salicylic acid is condensed with a short chain aldehyde (e.g. formaldehyde, acetaldehyde, propionaldehyde, butyraldehyde, iso-butyraldehyde, etc.) or ketone (e.g. acetone, methylethylketone, etc.) to produce a polyphenol dicarboxylate coupled at the position para to the hydroxyl group. This can be accomplished with either a homogenous or heterogeneous Bronsted acid, Lewis acid or solid acid catalyst (e.g. acid clay, cation exchange resin, zeolite, etc.) to produce a dicarboxylated bisphenol or heavier oligomer. The dicarboxylate is then decarboxylated to yield a polyphenol.

Example 3

Salicylic acid is prepared or isolated from a renewable source, e.g. wintergreen oil (methyl salicylate) or lignin, or produced via a biosynthetic route using biomass sugars or lignin as the substrate. Two equivalents of salicylic acid are condensed with one equivalent of an aldehyde or ketone utilizing an acid catalyst to produce a dicarboxylate coupled at the position para to the hydroxyl group. The dicarboxylate is decarboxylated to yield a polyphenol, for example, bisphenol A, bisphenol E, or bisphenol F.

The process comprising:

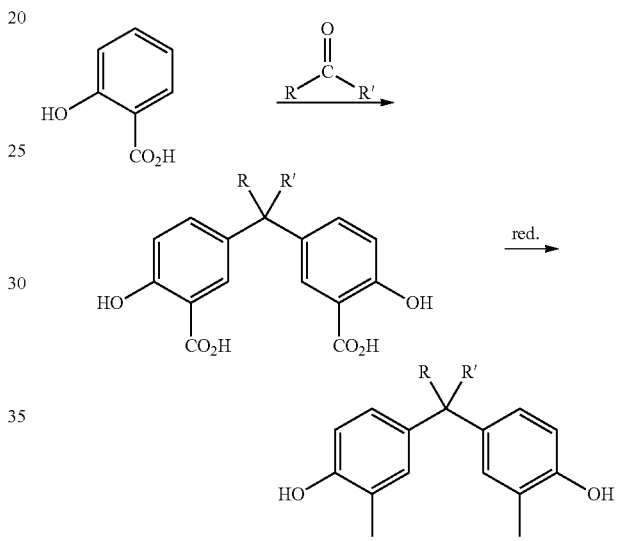

where R and R' of said carbonyl reactant are independently selected from the group consisting of hydrogen, alkyl having from 1-100 carbon atoms, substituted alkyl having from 1-100 carbon atoms, alkene having from 1-100 carbon atoms, substituted alkene having from 1-100 carbon atoms, alkenyl having from 1-100 carbon atoms, substituted alkenyl having from 1-100 carbon atoms, alkynyl having from 1-100 carbon atoms, substituted alkynyl having from 1-100 carbon atoms, alkyne having from 1-100 carbon atoms, substituted alkyne having from 1-100 carbon atoms, cyclic alkyl, substituted cyclic alkyl, aromatic, or substituted aromatic, or R and R' are mutually part of a ring system such as a cyclic ketone, e.g., cyclohexanone.

In one preferred embodiment, R and R' are different, resulting in an asymmetric bisphenol. When used in further processing, such asymmetric bisphenols can exhibit desirable qualities (e.g. low melting points) in resins, plastics, etc. made from them.

In another embodiment the process of the present invention can be used to produce bisphenols from functionalized salicylic acid. Such functionalization provides the benefits of for example, utilizing hydrophobic R groups to lower the melting point and lower any water uptake of resulting derivative resins In one embodiment the decarboxylation is accomplished with a catalyst at temperatures from about 100 to about 220 degrees C.

Figure 3:
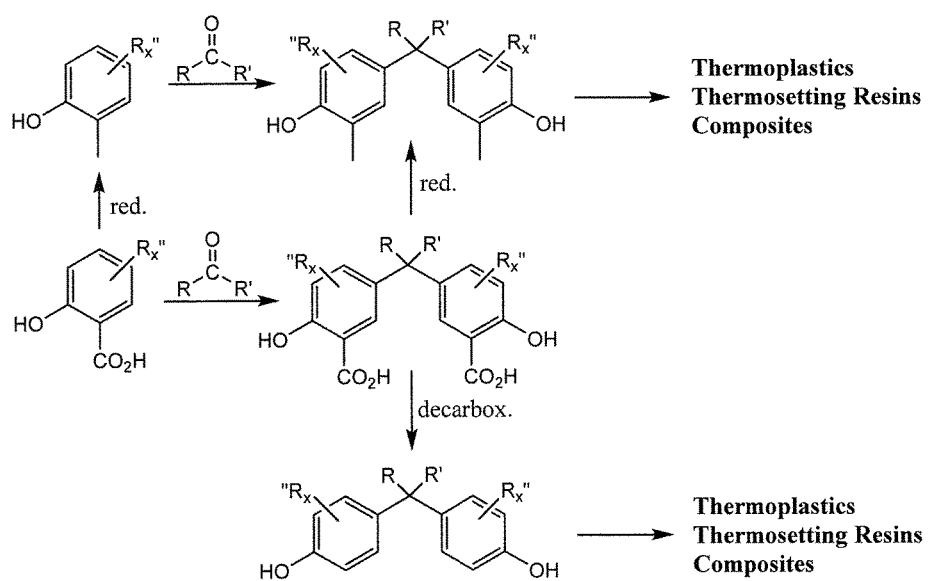
FIG. 3 is an illustration of synthetic schemes for producing resins, thermoplastics, and composite materials from bisphenols of generalized carboxylic acid functionalized phenols synthesized from renewable phenol sources according to embodiments of the invention.

A scheme for producing bisphenols and their products from functionalized salicylic acid (Tasks 2 & 3) is illustrated in FIG. 3. In the process a functionalized salicylic acid analogue having the formula:

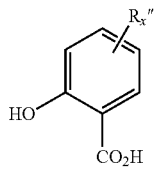

where R" is selected from alkyl, cycloalkyl, arene, ester, and alkoxy, and where x=1 to 3;
is reacted with an aldehyde/ketone having the formula:

where R and R' of said carbonyl reactant are independently selected from the group consisting of hydrogen, alkyl having from 1-100 carbon atoms, substituted alkyl having from 1-100 carbon atoms, alkene having from 1-100 carbon atoms, substituted alkene having from 1-100 carbon atoms, alkenyl having from 1-100 carbon atoms, substituted alkenyl having from 1-100 carbon atoms, alkynyl having from 1-100 carbon atoms, substituted alkynyl having from 1-100 carbon atoms, alkyne having from 1-100 carbon atoms, substituted alkyne having from 1-100 carbon atoms, cyclic alkyl, substituted cyclic alkyl, aromatic, or substituted aromatic, or R and R' are mutually part of a ring system such as a cyclic ketone, e.g., cyclohexanone, for example.

Functionalized salicylic acid can be prepared by the hydrogenation of the carboxylic acid group to an alcohol followed by the conversion of the alcohol group to an alkoxide by reaction with an alcohol and base. Any other variation in the structure could be a result of the original starting substrate, e.g. functional groups derived from an original lignin substrate.

Functionalized bisphenols can be prepared by the hydrogenation of the carboxylic acid group to an alcohol followed by the conversion of the alcohol group to an alkoxide by reaction with an alcohol and base. Any other variation in the structure would be a result of the original starting substrate, e.g. functional groups derived from an original lignin substrate.

In another embodiment, these same basic steps can be used to produce bisphenols from generalized carboxylic acid functionalized phenols, illustrated with the formula:

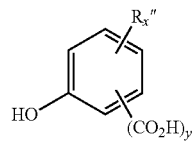

where R" is selected from alkyl, cycloalkyl, arene, alkoxy, and ester;
x is 0 to 3;
y is 1 to 4; and,
x+y is 1 to 5.

Figure 4:
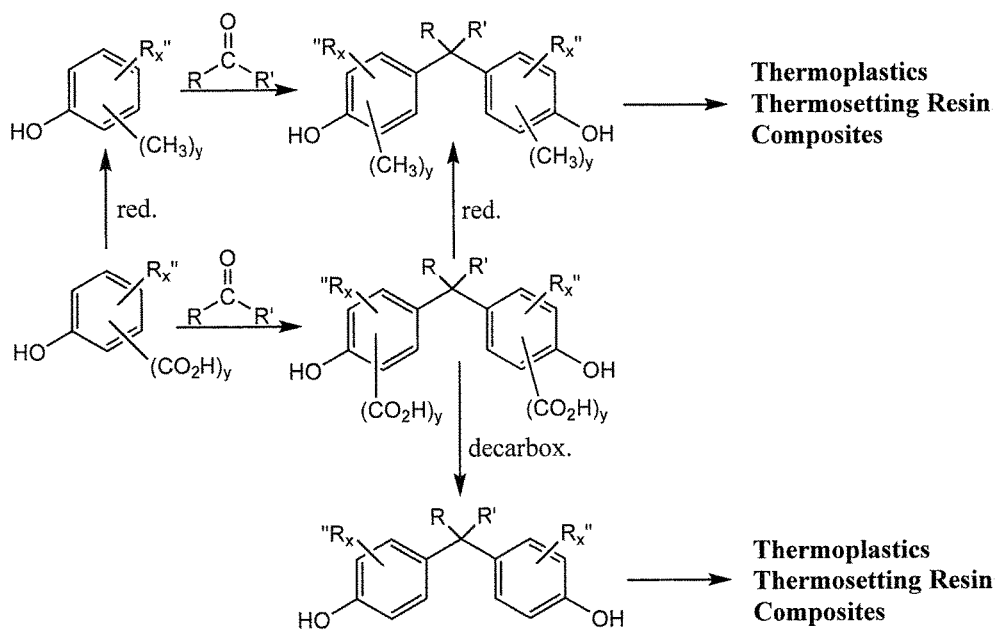
FIG. 4 is an illustration of synthetic schemes for producing resins, thermoplastics, and composite materials from bisphenols of ester functionalized phenols synthesized from renewable phenol sources according to embodiments of the invention.

A number of schemes for producing polyphenols and their products from such generalized carboxylic acid functionalized phenols according to the present invention are illustrated in FIG. 4. Suitable aldehydes or ketones have the formula:

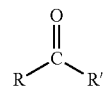

where R and R' of said carbonyl reactant are independently selected from the group consisting of hydrogen, alkyl having from 1-100 carbon atoms, substituted alkyl having from 1-100 carbon atoms, alkene having from 1-100 carbon atoms, substituted alkene having from 1-100 carbon atoms, alkenyl having from 1-100 carbon atoms, substituted alkenyl having from 1-100 carbon atoms, alkynyl having from 1-100 carbon atoms, substituted alkynyl having from 1-100 carbon atoms, alkyne having from 1-100 carbon atoms, substituted alkyne having from 1-100 carbon atoms, cyclic alkyl, substituted cyclic alkyl, aromatic, or substituted aromatic, or R and R' are mutually part of a ring system such as a cyclic ketone, e.g., cyclohexanone, for example.

Such generalized carboxylic acid functionalized phenols can be prepared by oxidation of lignin using molecular oxygen, nitrobenzene, hydrogen peroxide, or other strong oxidants.

Benefits of using such generalized carboxylic acid functionalized phenols include, for example, by converting a carboxylic acid into an ester, using base and an alcohol at elevated temperature, the carboxylic acid does not interfere with later chemistry, for example synthesis of thermosets or thermoplastics.

In another embodiment, the process of the current invention can be used to produce bisphenols from ester functionalized phenols, illustrated with the formula:

where $R^3$ is selected from alkyl, cycloalkyl, arene, or alkoxy, preferably an alkyl.

One such preferred embodiment using functionalized phenols is an ester of salicylic acid.

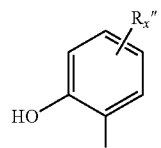

where R" is selected from alkyl, cycloalkyl, arene, alkoxy, and ester;

x is 0 to 3;

and, where $R^3$ is selected from hydrogen, alkyl, cycloalkyl, arene, or alkoxy, preferably an alkyl.

Another embodiment encompassing a number of schemes using ester functionalized phenols

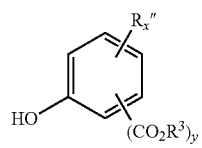

where R" is selected from alkyl, cycloalkyl, arene, alkoxy, and ester;

x is 0 to 3;

y is 1 to 4; and, x+y is 1 to 5.

where each $R^3$ is independently selected from hydrogen, alkyl, and arene.

A generalized scheme for producing bisphenols and their products from ester functionalized phenols is illustrated in FIG. 4.

Such ester functionalized phenols can be prepared by reaction of salicylic acid with an alcohol and a base at elevated temperatures.

Example 4

Decarboxylation of Salicylic Acid to o-cresol

In an oven-dried, 100 mL, three-necked, round bottom flask equipped with a stir bar, thermometer, septum, and condenser were added salicylic acid (0.9915 g, 7.18 mmol) and $Cu_2O$ (0.4233 g, 2.96 mmol). The apparatus was exposed to vacuum and flushed with nitrogen twice. N-Methylpyrrolidone (NMP) (15 mL) was added and the flask was placed into an oil bath at 170° C. Tetramethylethylenediamine (TMEDA) (0.7150 g, 6.15 mmol) was added via syringe and the reaction was stirred at 185° C. (oil bath) for 20 hours. The flask was air-cooled to room temperature, quenched with 60 mL 1 N HCl(aq), and allowed to stir for 5 minutes. The resulting mixture was filtered through Celite and the reaction vessel was rinsed with 3×5 mL EtOAc. The filtrate was extracted with 3×50 mL EtOAc and the combined organic layers were washed with water (50 mL) and brine (2×50 mL). The organic layer was then dried over $MgSO_4$ for 5 minutes, filtered, and concentrated by rotary evaporation to give crude phenol.

Example 5

Methyl salicylate is isolated from a natural source (e.g. wintergreen oil). The methyl salicylate is converted to salicylic acid by treatment with a base.

Example 6

Synthesis of 5,5'-methylenebis(2-hydroxybenzoic acid)

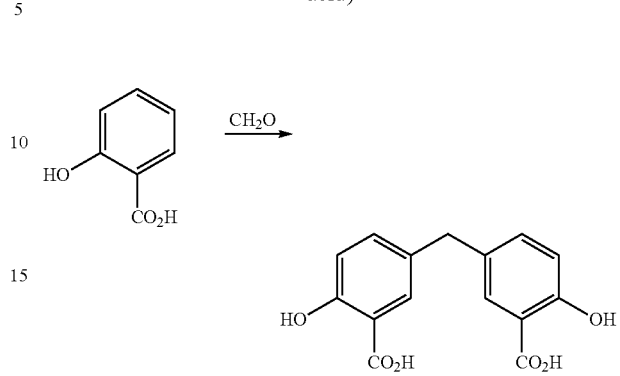

In a round bottom flask salicylic acid (10.04 g, 72 mmol) was dissolved in acetic acid (120 mL). To this mixture 30% formaldehyde (6 g, 43 mmol) was added. Next, conc. sulfuric acid was added and the reaction was refluxed under nitrogen overnight. Once the reaction was cooled the solid was filtered and washed with additional acetic acid to remove any unreacted salicylic acid. 8.7 grams of off white powder were obtained (84% yield).

Example 7

In Task 3 of the process of this invention, the bisphenol is thermally decarboxylated in the presence of a catalyst (e.g. soda lime, copper salts, silver salts, or various high boiling amines). This process can be conducted either through conventional heating, or greatly facilitated by microwave heating, either in a solvent or as a solid. The resulting bisphenols can be purified by crystallization, sublimation, chromatography, etc.

Preferred catalysts are copper salts or chelating amine ligand. Preferred temperatures are from about 100 to about 220 degrees C.

Example 8

Decarboxylation of 5,5'-methylenebis(2-hydroxybenzoic acid)

In an oven-dried, 100 mL, three-necked, round bottom flask equipped with a stir bar, thermometer, septum, and condenser were added 5,5'-methylenebis(2-hydroxybenzoic acid) (1.453 g, 5.04 mmol) and $Cu_2O$ (0.723 g, 5.05 mmol). The apparatus was exposed to vacuum and flushed with nitrogen twice. NMP (15 mL) was added and the flask was placed into an oil bath at 170° C. TMEDA (1.310 g, 11.3 mmol) was added via syringe and the reaction stirred at 185° C. (oil bath) for 20 hours. The flask was air-cooled to room temperature, quenched with 60 mL 1 N HCl(aq), and allowed to stir for 5 minutes. The resulting mixture was filtered through Celite and the reaction vessel was rinsed with 3×5 mL EtOAc. The filtrate was extracted with 3×50 mL EtOAc and the combined organic layers were washed with water (50 mL) and brine (2×50 mL). The organic layer was then dried over MgSO4 for 5 minutes, filtered, and concentrated by rotary evaporation to give the bisphenol.

Example 9

Synthesis of 5,5'-Isopropylidenedisalicylic Acid

A mixture of salicylic acid, acetone, and 60% sulfuric acid is heated under gentle reflux for 10-12 hr. with constant stirring. It is allowed to cool and is filtered, and the residue is washed with cold water and air dried. Unchanged salicylic acid is removed by adding the powdered product to boiling water, with constant stirring, filtering while hot, and allowing the residue to dry in air. Purification is effected by dissolving the crude product in an excess of hot 95% ethanol, treating with activated charcoal, filtering, and reprecipitating with cold water. The material is dried in a vacuum desiccator (CaCl). See, J. Med. Chem. 1965, 8 (3), 405.

Example 10

Decarboxylation of 5,5-(propane-2,2-diyl)bis(2-hydroxybenzoic acid)

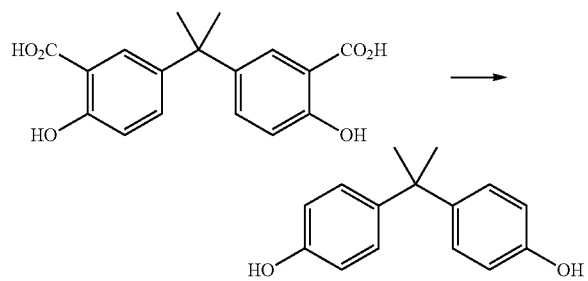

A mixture of 5,5'-(propane-2,2-diyl)bis(2-hydroxybenzoic acid) (2.0 g, 6.3 mmol), $Cu_2O$ (0.75 g, 5.2 mmol, 0.8 eq) and tetramethylethylenediamine (1.6 mL, 11 mmol) in 30 mL N-methyl-2-pyrrolidinone was heated to 180° C. and stirred for 48 hours. The mixture was then allowed to cool and filtered through Celite. The filtrate was poured into 200 mL 1N HCl with ice. This was extracted with 2×150 mL ether. The combined extracts were washed with water and dried ($MgSO_4$) then concentrated in vacuum to give 1.06 grams of bisphenol A (74%), pure by NMR. $^1H$ NMR ($CDCl_3$): 7.10 (d, 4H), 6.73 (d, 4H), 1.63 (s, 6H).

Example 11

Salicylic acid is hydrogenated at an elevated temperature and pressure to produce cresol. The cresol is allowed to condense with a short chain aldehyde or ketone (e.g. formaldehyde, acetaldehyde, acetone, methylethylketone, propionaldehyde, etc.) to produce a bisphenol A analog.

Example 12

Synthesis of 4,4'-(ethane-1,1-diyl)bis(2-methylphenol)

o-cresol (300 mL, 2.86 mol, 3.8 eq) was cooled to <5° C. under mechanical stirring while acetaldehyde (42 mL, 0.75 mol) was added. 30 mL ether was added to dissolve the solids. To this was added 3 mL conc HCl. The temperature rises to 20° C. before falling back to 5° C. The clear pinkish solution was stirred for 18 hours at room temperature then transferred to a 1 L single necked round bottom flask. Excess o-cresol was removed under high vacuum at 100° C. to give 237.25 grams of clear thick oil. This was distilled in a Kugelrohr apparatus to give 178.91 grams of a clear glassy material (97%). This is a mixture of 18 mole % of the 2,4'-isomer along with about 10 mole % of the trimer. 1H NMR (CDCl3): 6.98 (s, 2H), 6.96 (d, 2H), 6.70 (d, 2H), 4.66 (br s, 2H), 3.98 (q, 1H), 2.23 (s, 6H0, 1.57 (d, 3H).

Example 13

In the process of Example 1, the dicarboxylate is hydrogenated, resulting in reduction of the carboxyl groups to methyl groups.

Example 14

Production of resin adds an additional step (Task 4) to the process of this invention in which polyphenols prepared in (Task 3) are converted to a variety of resins (e.g. cyanate esters, epoxides, etc.).

Example 15

Synthesis of 4,4'-(ethane-1,1-diyl)bis((1-cyanato-2-methylbenzene)

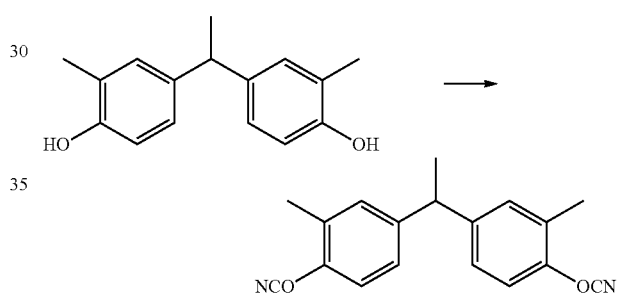

A solution of 4,4'-(ethane-1,1-diyl)bis(2-methylphenol) (78.48 g, 0.324 mol) and cyanogen bromide (80 g, 0.755 mol, 2.3 eq) in 1 L ether was cooled to −5° C. (ice salt bath) while a solution of triethylamine (108 mL, 0.776 mol, 2.4 eq) in 100 mL ether was added dropwise over 30 minutes. The mixture was allowed to warm to room temperature and stirred for three hours then washed with water, dried (MgSO4) and concentrated in vacuum to give 102.07 grams of an off-white solid. This was chromatographed on Silica gel using methylene chloride to give 45.27 grams of a white solid (48%). Mp. 72.1° C. 1H NMR (CDCl3): 7.34 (d, 2H), 7.09 (d, 2H), 7.04 (s, 2H), 4.10 (q, 1H), 2.28 (s, 6H), 1.60 (d, 3H).

Example 16

Polyphenols prepared in Task 3 are directly converted to thermoplastics (Task 5) including polycarbonates, polysulfones, polyethers, and polyarylates.

Example 17

Polyphenols prepared in Task 3 can be directly converted to thermoplastics (Task 5) including poly carbonates by reaction with dimethyl carbonate, diphenyl carbonate, phosgene, triphosgene, p-nitrophenyl chloroformate, other chloroformates, or other phosgene surrogates.

Example 18

Polyphenols prepared in Task 3 can be directly converted to thermoplastics (Task 5) including poly carbonates by reaction with diphenyl carbonate and a zinc catalyst.

Example 19

Thermoplastics produced in Task 5 are either utilized in a pure form or are combined with at least one support material to produce a composite.

Example 20

Polyphenols (prepared in Task 3) are converted using a soluble base and cyanogen halide(s) or pseudohalides to produce cyanate ester resins.

Example 21

Polymerizing said polyphenols (prepared in Task 3) by thermal or chemical methods or with irradiation to produce high molecular weight thermoplastics.

Example 22

Production of thermosets (Task 6) wherein resins prepared in Task 4 are cross-linked to form high molecular weight thermosets.

Example 23

Production of thermosets (Task 6) in which resins from Task 4 (e.g. cyanate esters, epoxides) are thermally cross-linked to produce network polymer thermosets.

Example 24

Resins from Task 4 are combined with fibers (e.g. glass, carbon) or other support materials and cured through various methods including the use of heat and/or catalysts to produce a mixture; curing said mixture to produce composite materials (Task 7).

Example 25

Thermoplastics are either utilized in a pure form or are combined with at least one support material to produce a composite material (Task 8). Composites may include blends of thermoplastics and thermoset resins.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

The invention claimed is:

1. A method for synthesizing polyphenol compounds from a renewable, ortho-substituted phenol source, comprising:
   a) condensing a carbonyl reactant with said renewable ortho-substituted phenol utilizing at least one acid catalyst to form a polyphenol;
   said renewable ortho-substituted phenol having the formula:

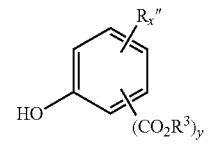

where each R″ is independently selected from alkyl, cycloalkyl, arene, alkoxy, and OH;
each $R^3$ is independently selected from hydrogen, alkyl, cycloalkyl, arene, or alkoxy;
x is 0 to 3;
y is 0 to 4;
x+y is 1 to 5; and,
where one of said x+y substituent groups is ortho to the hydroxy group on said phenol, and
said carbonyl reactant having the formula:

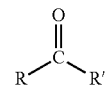

where R and R' are each independently selected from the group consisting of hydrogen, an aliphatic group or an aromatic group or are mutually part of a ring system;
   b) where y is greater than zero, modifying said polyphenols by reducing said ($CO_2R^3$) groups to either hydrogen or a methyl group.

2. The method of claim 1 wherein
R and R' of said carbonyl reactant are independently selected from the group consisting of hydrogen, alkyl having from 1-100 carbon atoms, substituted alkyl having from 1-100 carbon atoms, alkene having from 1-100 carbon atoms, substituted alkene having from 1-100 carbon atoms, alkenyl having from 1-100 carbon atoms, substituted alkenyl having from 1-100 carbon atoms, alkynyl having from 1-100 carbon atoms, substituted alkynyl having from 1-100 carbon atoms, alkyne having from 1-100 carbon atoms, substituted alkyne having from 1-100 carbon atoms, cyclic alkyl, substituted cyclic alkyl, aromatic, or substituted aromatic.

3. The method of claim 1 wherein one equivalent of a carbonyl reactant is condensed with two equivalents of said renewable ortho-substituted phenol.

4. The method of claim 3 wherein said polyphenol compounds are bisphenols.

5. The method according to claim 1 wherein x is 0 to 3 and y is 1 to 4.

6. The method of claim 5 wherein said renewable, ortho-substituted phenol source is salicylic acid.

7. The method of claim 1 wherein said renewable, ortho-substituted phenol source is methyl salicylate.

8. The method according to claim 1 wherein x is 1 to 3 and y is 0 to 4.

9. The method according to claim 8 wherein said renewable, ortho-substituted phenol source is o-cresol.

10. The method according to claim 1, further comprising converting said polyphenols to polymers.

11. The method according to claim 10, wherein said polymers are thermosetting resins or thermoplastics.

12. The method according to claim 10, wherein said polymers are resins, epoxies, polycarbonates, polyethers, poly ether ether ketones (PEEK), polyarylates, polyesters, epoxides, polysulfones, polyester-styrene, alkylphenolic polymers, polyoxalates, polyalylates, high temperature thermosets, cyanate esters, epoxy resins, or benzoxazines.

13. The method of claim 11 wherein said thermoplastic is a polycarbonate and wherein said polycarbonate is produced by reaction of said polyphenols with a carbonate source selected from the group consisting of carbonates, diphenyl carbonate, chloroformates, p-nitrophenyl chloroformate, phosgene, triphosgene, or phosgene surrogates.

14. The method according to claim 11, wherein said polymers are cyanate ester resins produced by reacting said polyphenols with a soluble base and cyanogen halide or pseudohalide.

15. The method according to claim 11, further comprising polymerizing said thermosetting resins to produce high molecular weight thermoset materials.

16. The method according to claim 11, further comprising polymerizing said thermosetting resins with glass fibers, carbon fibers, other support materials, or combinations thereof to produce a mixture and curing said mixture to produce composite materials.

17. The method according to claim 11, further comprising utilizing said thermoplastics in a pure state or combined with at least one support material and/or thermoset material to produce composite materials.

* * * * *